United States Patent
Neuberger et al.

(10) Patent No.: US 6,527,764 B1
(45) Date of Patent: Mar. 4, 2003

(54) DEVICE AND METHOD FOR LASER BIOMODULATION IN PDT/SURGERY

(75) Inventors: Wolfgang Neuberger, F.T. Labuan (MY); Stefan Spaniol, Bonn (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/453,338

(22) Filed: Dec. 2, 1999

(51) Int. Cl.[7] .............................................. A61B 18/18
(52) U.S. Cl. ............................ 606/10; 606/13; 606/16; 607/89
(58) Field of Search ................... 606/3, 7–10, 13–16; 607/88, 89; 385/15, 53, 76, 88–92, 126–128

(56) References Cited

U.S. PATENT DOCUMENTS

| | | | | |
|---|---|---|---|---|
| 4,266,549 A | * | 5/1981 | Kimura | 128/303.1 |
| 4,583,539 A | * | 4/1986 | Karlin et al. | 128/303.1 |
| 5,207,576 A | * | 5/1993 | Vassiliadis et al. | 433/215 |
| 5,275,594 A | * | 1/1994 | Baker et al. | 606/12 |
| 5,290,275 A | * | 3/1994 | Kittrell et al. | 606/15 |
| 5,325,393 A | * | 6/1994 | Nighan, Jr. et al. | 372/97 |
| 5,350,375 A | * | 9/1994 | Deckelbaum et al. | 606/7 |
| 5,540,676 A | * | 7/1996 | Freiberg | 606/3 |
| 5,738,679 A | * | 4/1998 | Daikuzono | 606/11 |
| 5,746,735 A | * | 5/1998 | Furumoto et al. | 606/9 |
| 5,938,657 A | * | 8/1999 | Assa et al. | 606/9 |
| 6,074,382 A | * | 6/2000 | Asah et al. | 606/9 |
| 6,160,943 A | * | 12/2000 | Davis et al. | 385/126 |

FOREIGN PATENT DOCUMENTS

| | | | | |
|---|---|---|---|---|
| FR | 25 98 608 A | * | 11/1987 | A61B/17/36 |
| SU | 10 73 914 A | * | 6/1985 | A61B/17/00 |

* cited by examiner

*Primary Examiner*—Linda C. M. Dvorak
*Assistant Examiner*—A. Farah
(74) *Attorney, Agent, or Firm*—BJ Associates; Bolesh J. Skutnik

(57) ABSTRACT

The present invention provides a device and method for a laser treatment that couples surgical or activating laser power with a biomodulating power to enhance proper tissue healing and regeneration after treatment. This treatment is achieved using an optical fiber system delivering laser power from two separate laser sources. One source provides laser energy at a power level and density suitable for the surgical or activation action desired. The second source produces laser power at a wavelength suitable for producing biomodulating effects in the treated tissue. Biomodulation treatment of the tissue promotes cellular healing and regeneration and ensures that proper healing occurs. In addition, the present invention describes a method by which the device is used for treatment. The surgical or activating laser energy is applied to a site as the device is passed over the treatment area. During this treatment, the device also emits a biomodulating treatment beam onto the site over which the first beam has already passed. The device in this manner systematically performs a surgical or activation action and then follows immediately with a healing action, enhancing the success of the treatment by ensuring that the treated tissue heals quickly and properly.

9 Claims, 6 Drawing Sheets

DEVICE AND METHOD FOR LASER BIOMODULATION IN PDT/SURGERY

BACKGROUND OF THE INVENTION

1. Field of the Invention

The invention relates generally to medical laser treatments and more specifically to laser treatments performed in conjunction with simultaneous biomodulation effects: biostimulation and and/or biosuppression (and subsequent immunostimulation) such as cellular growth or repression.

2. Invention Disclosure Statement

Laser treatments such as laser surgery and Photodynamic Therapy (PDT) have gained acceptance in the medical community as competent and effective medical treatment modalities. Both treatments employ a high-power laser energy to effectuate the procedure. In comparison, low power laser energy can be used to elicit cellular responses helpful in promoting healing. These cellular responses and any practical applications they might provide have been undefined. The effect of low-power laser therapy appears to vary with wavelength and exposure time in an essentially unexplained manner.

It was recently discovered that the absorption of radiation by chromophores, light absorbing structures located within cells, can promote changes in that cell's energy production cycle. An increase in the cellular energy level will in turn result in cellular responses such as increased beneficial cell regeneration and growth. Conversely, a decrease in the cell's energy production cycle will have the opposite effect by decreasing regeneration and slowing growth.

Biostimulation systems for wound healing are known. For example, U.S. Pat. No. 4,612,604 describes a biostimulation system wherein a uniform beam of polarized light generated by a lamp is projected onto the treatment area, however, the invention is limited. First, the device employed to deliver the biostimulating energy is cumbersome. The device employs a lamp as the light source which projects its light through a lens and onto a projector (similar to an overhead projector device). In addition, the system is enclosed in a housing structure cooled by a fan. The overall size of the device makes it impractical for precise or mobile applications. Second, The light is emitted from a lamp and projected onto the treatment site. The application is therefore, broad and highly dependent on the distance the source is placed from the treatment site, thereby further cutting down on the system's mobility. Therefore, it follows that the system described provides only a broad biostimulating action.

U.S. Pat. No. 4,930,504 describes a biostimulation device that employs monochromatic radiation at a variety of wavelengths to stimulate healing in various tissues. The system however solely produces biostimulation effects, it does not provide for any coordinate treatment (one that causes cellular damage). Treatment is administered only after damage to the tissue has occurred. It is beneficial to be able to perform both coordinate treatments and biostimulation with a single device. The system described cannot accommodate such a variation and is therefore limited to its specific application.

Surgical laser systems contain visible aiming beams of several mW of power. Sometimes these aiming beams fall within a wavelength range suitable to be absorbed in one of the cell's major chromophores. However, any amount of biostimulation that is obtained by this aiming beam, is inadvertent, undetected and uncontrolled. Beneficial effects, if any, caused by this unscheduled exposure are accidental. Effective biostimulation requires that consistent power be employed in a regulated and controlled manner. No laser system exists which can administer the correct dosage of biostimulating laser power together with a component to apply the correct low-level laser power thoroughly over the required surface or tissue areas, to purposely complement a surgical and/or PDT application.

For example, U.S. Pat. No. 5,289,557 describes a medical laser system that employs a visible laser-aiming beam. The aiming beam is produced at a wavelength within the range of biostimulating light. However, any biostimulating effects caused by the aiming beam are inadvertent, unintended and uncontrolled. For effective biostimulation the wavelength of light used in the treatment must be carefully selected and the system must supply the correct irradiation dosage (dosage denoting power density and treatment time). Systems not employing these parameters will be both inconsistent and ineffective for and thus inapplicable to biostimulation.

A system that employs both an operating beam output as well as a 'simultaneous' biomodulating (comprised of either a biostimulating or a biosuppressing/immunostimulating action effecting cellular activity) low-power laser output would be beneficial. The system must be significantly versatile yet precise so that effective treatment can be administered.

BRIEF SUMMARY OF THE INVENTION

It is an aim of the present invention to provide a medical laser device and method for surgical or activating laser treatments that simultaneously incorporates a biomodulating component to ensure enhanced tissue healing and regeneration after treatment is administered.

It is another aim of the present invention to couple biomodulating laser energy delivery with photodynamic therapy to enhance tissue healing properties after treatment is administered.

It is a further aim of the present invention to couple biomodulating laser energy delivery with the activation of photosensitizers to enhance tissue healing properties after treatment is administered.

It is still another aim of the present invention to provide a method by which the laser system can be used effectively to apply surgical or activation laser power simultaneously with biomodulating power.

Briefly stated, the present invention provides a device and method for laser treatment that couples surgical or activating laser power with biomodulating power to enhance proper tissue healing and regeneration in conjunction with treatment. This treatment is achieved using an optical fiber system delivering laser power from two separate laser sources. One source provides laser energy at a power level and density suitable for the surgical or activation action desired. The second source produces laser power at a wavelength suitable for producing biomodulating effects in the treated tissue. Biomodulation treatment of the tissue promotes cellular healing and regeneration and ensures that proper healing occurs. In addition, the present invention describes a method by which the device is used for treatment. The main operating beam is applied to a site as the device is passed over the treatment area. During this treatment, the device also emits a biomodulating treatment beam onto the site over which the first beam has already passed. The device in this manner systematically performs a very high energy surgical or activation action and then applies immediately a healing action, enhancing the success of the treatment by ensuring that the treated tissue heals quickly and properly.

The above, and other objects, features and advantages of the present invention will become apparent from the following description read in conjunction with the accompanying drawings, in which like reference numbers in different drawings denote like items.

DISCLOSURE OF PREFERRED EMBODIMENTS

The present invention allows users to administer laser energy to a treatment area to perform laser surgery procedures such as photodynamic therapy and chemical activation. Simultaneously, through the same instrument biomodulating laser power is introduced to enhance healing of the tissue. Biomodulation includes the use of either a biostimulating wavelength or a biosuppressive/immunostimulating wavelength. Biostimulating a treatment area results in an increase in beneficial cellular regeneration and growth at that site. Conversely, biosuppressing a treatment area will decrease cellular regeneration and growth at that site. Biosuppression can lead to immunostimulation where an increased immunological activity is produced. As a result of such active therapy, healing at the treatment site will be expedited allowing for a more successful treatment.

Figure 1:
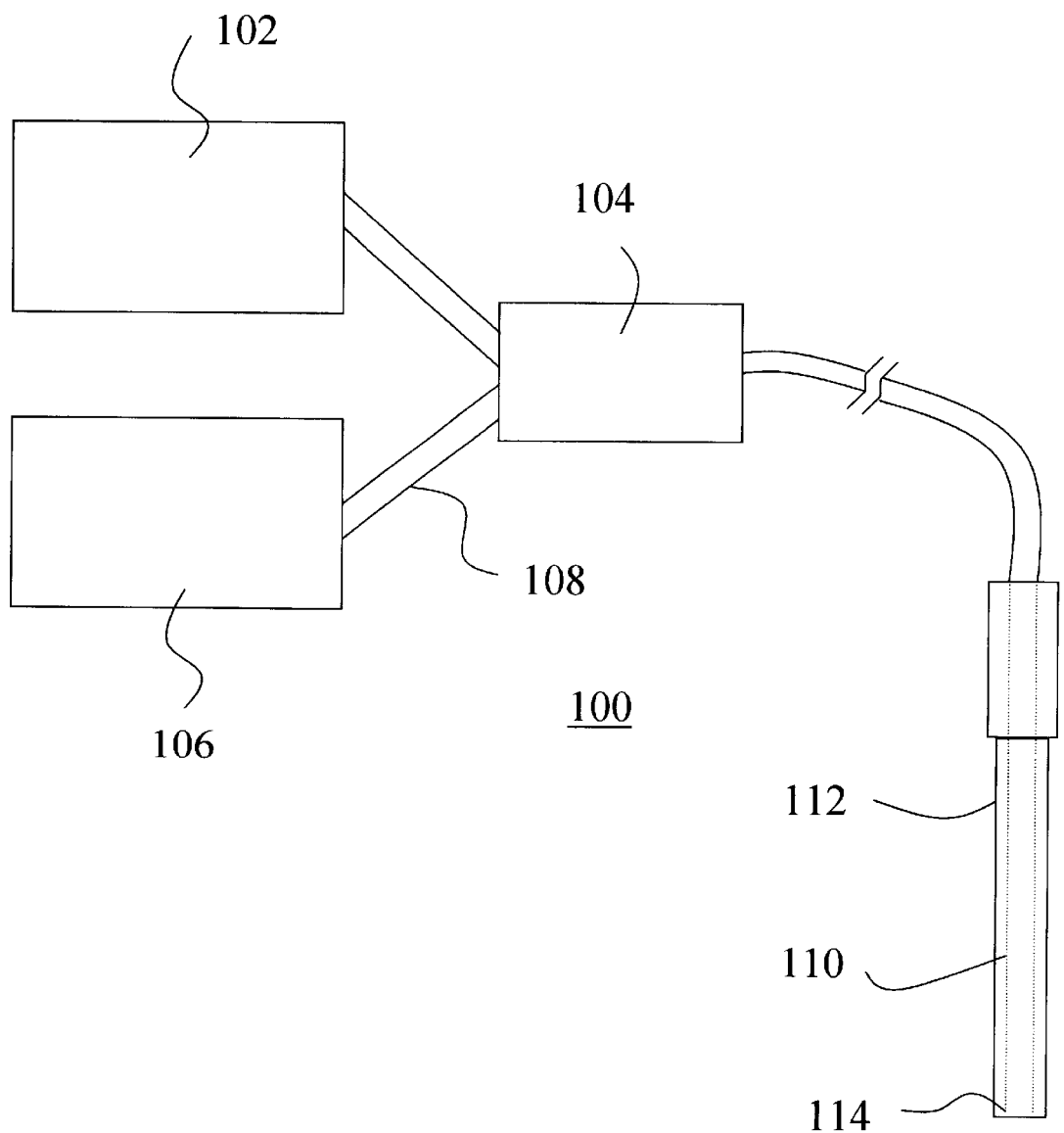
FIG. 1 is a schematic diagram illustrating the composition of the laser system.

FIG. 1 illustrates schematically how laser system 100 is structured. In this embodiment of the invention, two separate laser sources 102 and 106 supply the power for the treatments. Laser source 102 provides laser energy, main operating beam, directed towards primary laser applications such as laser surgery, PDT treatment, or chemical activation. The energy supplied by source 102 will vary depending on the required treatment. Laser source 106 produces laser energy at wavelengths specific for biomodulation. For many cases, laser energy produced with a constant wavelength of 635 nm provides suitable biomodulation energy.

The outputs from laser sources 102 and 106 are directed into optical fibers 108. Each fiber 108 has a solid core and is composed of silica. The laser energy is delivered to optical coupler 104. Optical coupler 104 combines laser energy from laser sources 102 and 106 into optical output structure 110. In a variation of the invention, optical coupler 104 can be integrated with optical output structure 110 such that the two structures can operate as one compact unit allowing more versatile administration of the treatment.

Some examples of the structure of optical output structure 110 can be seen in FIG. 2. Optical output structure 110 delivers laser energy from laser sources 102 and 106 to the treatment site. Optical output structure 110 passes through hand piece 112. Hand piece 112 provides for easier treatment application by preventing bending or twisting of optical output structure 110 thereby allowing users to hold optical output structure 110 in a fixed orientation when treating.

The laser energy from laser sources 102 and 106 exit system 100 from distal output end 114 of hand piece 112. Depending on the structure of optical output structure 110 (see FIG. 2), the orientation of the delivered laser power can be important to the success of the treatment. Therefore, it is helpful to have on distal output end 114 of hand piece 112 some indication of how optical output structure 110 is aligned. For example, if treatment is administered as illustrated in FIG. 3, an arrow signifying the direction of treatment inscribed on distal output end 114 of hand piece 112 would ensure proper application.

FIG. 2 illustrates variations in the set-up of the optical output hand piece employed to deliver the treatment laser energy. FIG. 2a shows one embodiment of the output structure wherein it is comprised of a multi-core fiber with fiber jacket 204 surrounding cladding layer 208. Embedded in cladding layer 208 and running parallel to the axis of the multi-core fiber are two solid cores, 202 and 206. Core 206 functions by delivering the laser power needed for surgical and activation procedures. Core 206 must therefore be of a diameter sufficient to carry this power. Core 202 functions in delivering low-power laser energy needed for providing biomodulation effects at the treatment site. The diameter of core 202 is therefore less than that of core 206. In this particular embodiment, the orientation of the multi-core fiber is crucial because core 202 and core 206 are at a specific, fixed distance and placement from one another. The user must take care to ensure proper application of the primary laser energy and the stimulating energy to the proper treatment areas.

In a multi-core embodiment the Numerical Aperture (NA) can differ for each core such that the core with the lower NA is set to deliver a more focused beam with a smaller amount of dispersion, that is easier to apply and control. Conversely, the core with the higher NA delivers a lower power, larger angle and more disperse biomodulating laser energy. The larger the area the biomodulating laser energy is exposed to, the more coverage is obtained during treatment. To have such a device with varying NA values as in the embodiments shown in FIG. 2, both cores are contained within the same cladding material, thus each core must be composed of a different material. Each core material will have a different index of refraction.

Figure 2A:
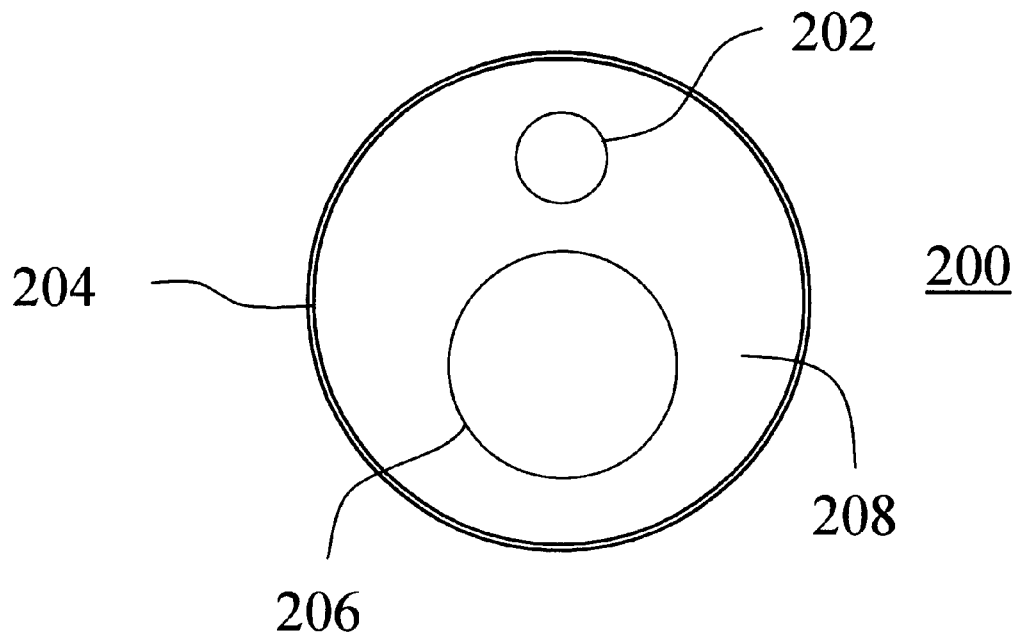
FIG. 2 is comprised of FIGS. 2a, 2b, 2c and 2d. These show diagrams of possible optical fiber configurations and orientations designed to deliver both primary laser radiation as well as low-level, biomodulating laser power.
Figure 2B:
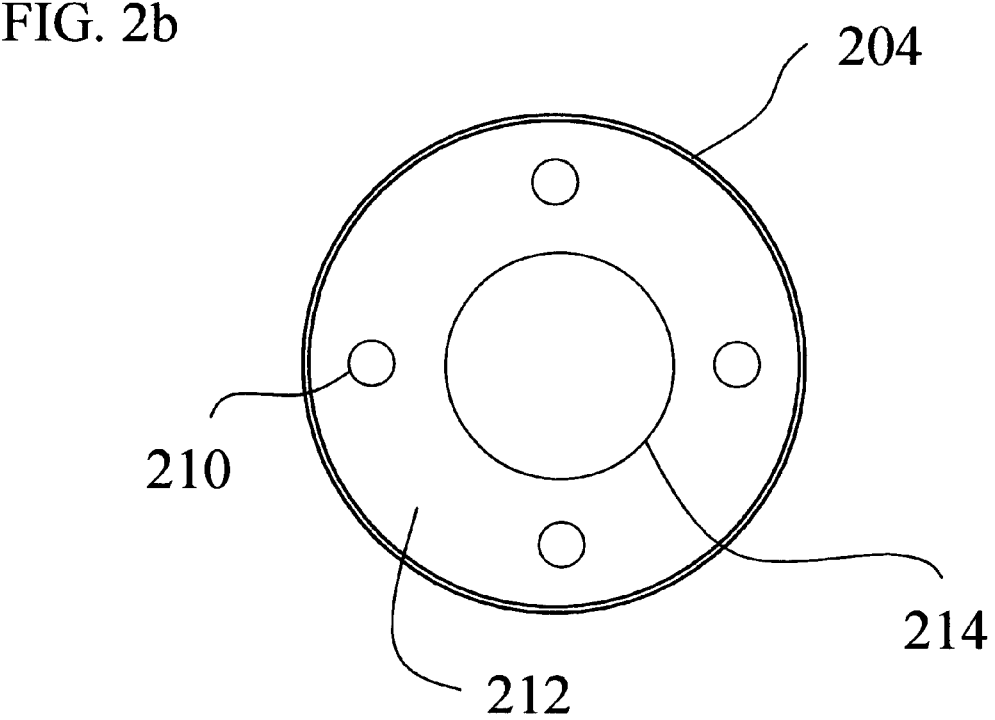
Figure 3:
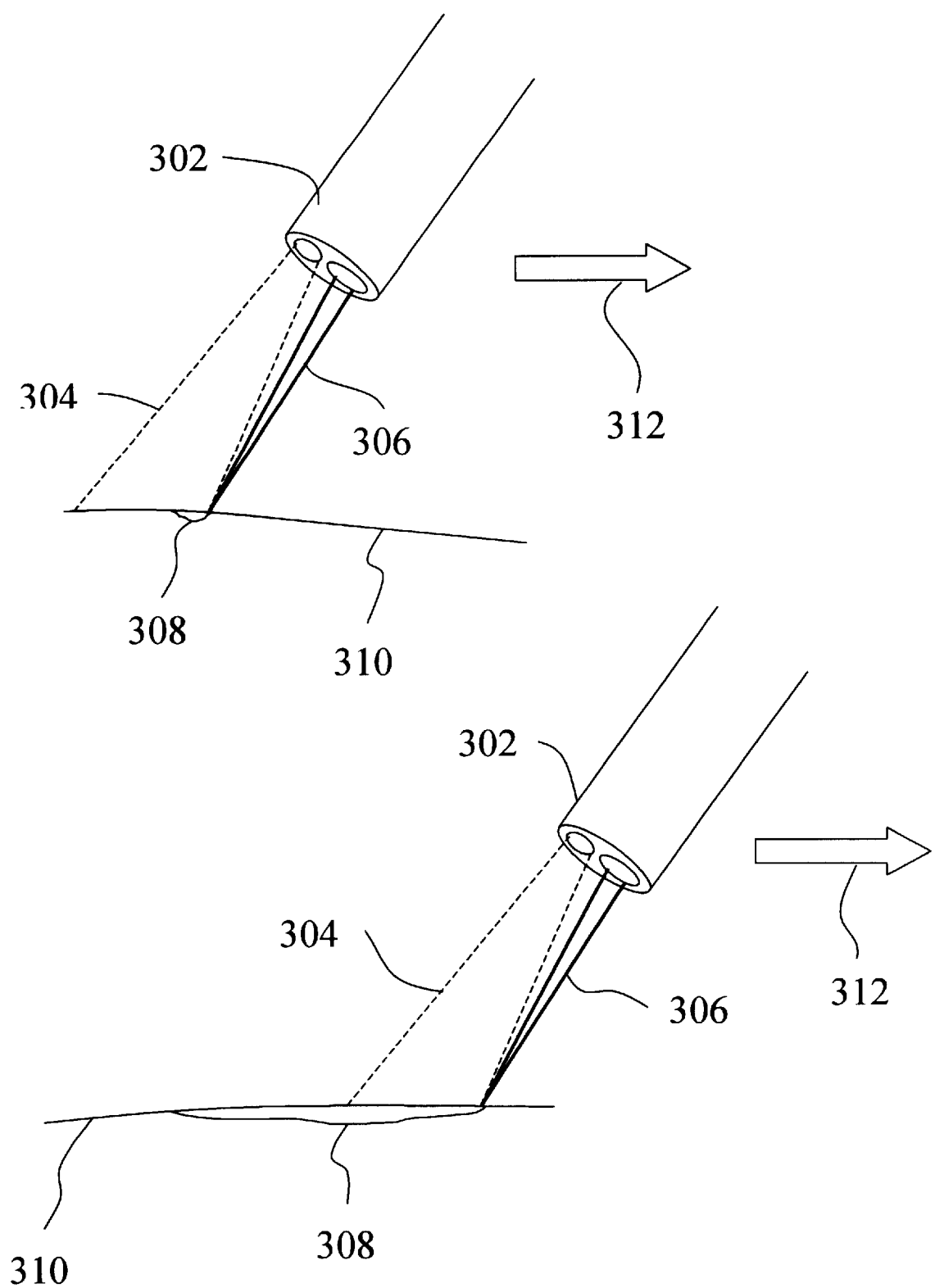
FIG. 3 is a stepwise depiction of how the laser system is used in treatment.

FIG. 2b shows another multi-core embodiment of the optical output hand piece wherein fiber jacket 204 surrounds cladding 212. Embedded in cladding 212 and running parallel to the axis of the multi-core fiber are multiple cores 210 and 214. Core 214, centrally situated in the fiber, delivers the main operating beam. Multiple cores 210, spaced evenly around core 214, function in delivering the laser energy needed for providing biomodulation effects at the treatment site. Cores 210 deliver a lower power laser than does core 214, and therefore the diameters of cores 210 are smaller.

Figure 2C:
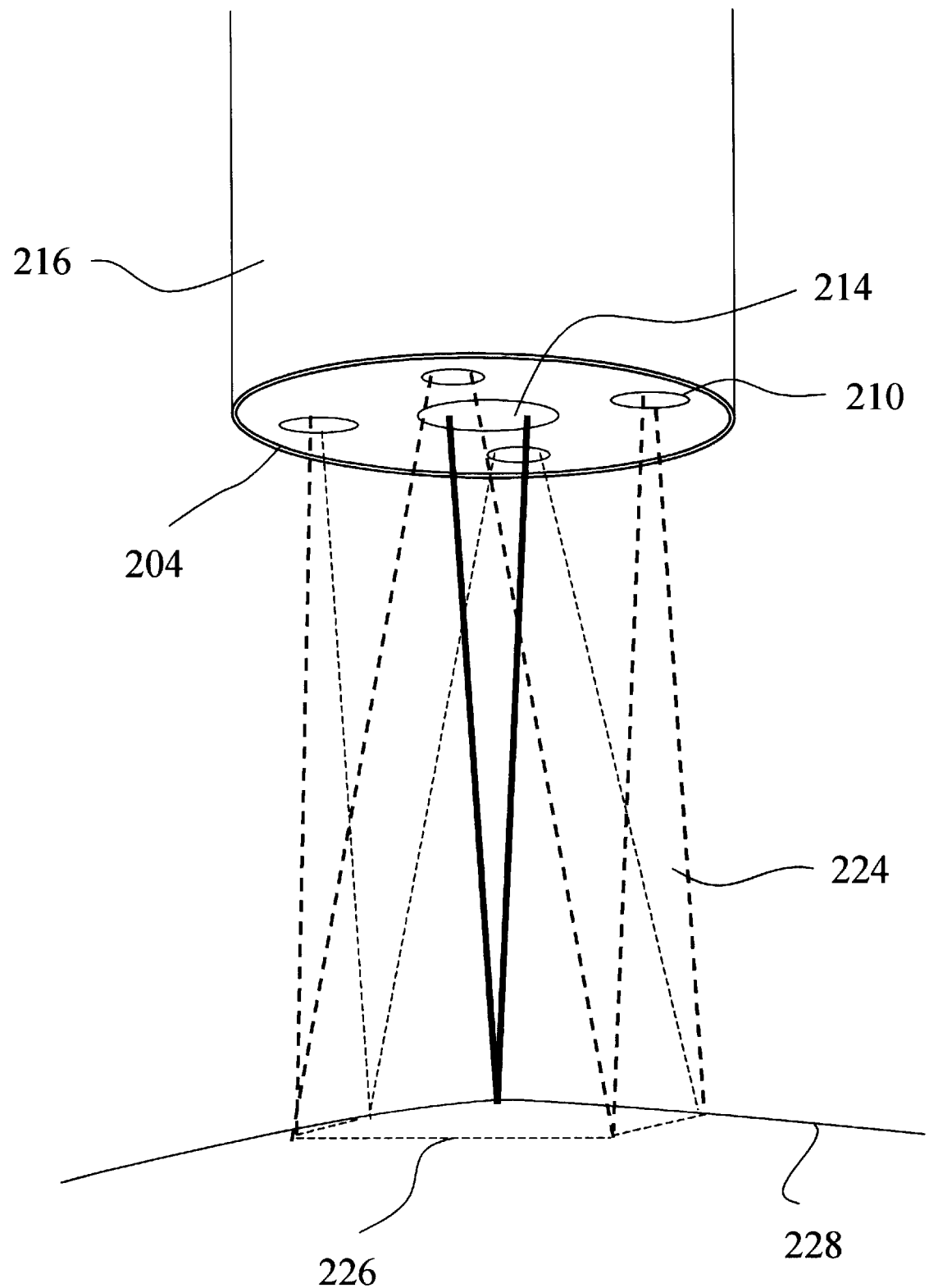

The embodiment illustrated in FIG. 2b is less dependent on the orientation of fiber 200 during treatment. A different perspective of the optical output structure is shown in FIG. 2c. This figure shows the biomodulating laser power being collectively emitted from cores 210, within multi-core optical fiber 216 that effectively surrounds the area covered by laser power emitted from core 214, at treatment site 228. Therefore, any placement of cores 210 around core 214 will suffice for stimulation.

Figure 2D:
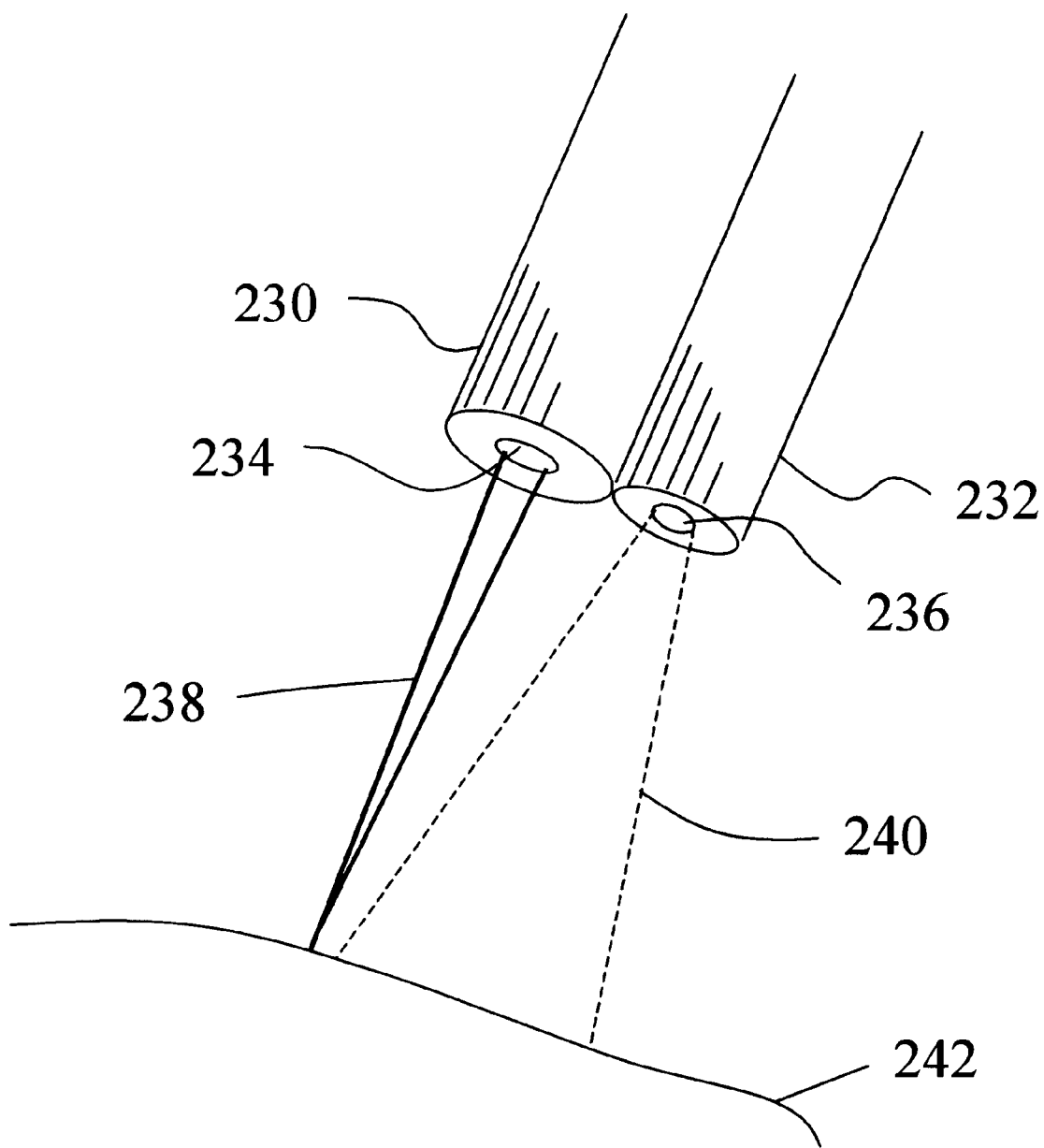

FIG. 2d shows an embodiment of the optical output hand piece wherein two separate optical fibers 230 and 232 are employed. Optical fiber 230 with larger core 234 delivers laser energy 238 sufficient to perform surgical or activation procedures. Optical fiber 232 with smaller core 236 functions in delivering low-power biomodulating laser energy 240 to treatment site 241. In multiple fiber embodiments of the invention, each fiber must be appropriately optically connected to its corresponding laser source such that delivery of the high power laser energy can occur in concert with the delivery of the low power laser energy.

FIG. 3 shows a stepwise depiction of the laser system being used for treatment. This figure illustrates use of the device to conduct simultaneous laser surgery and biostimulation. In the procedure, multi-core optical fiber 302 delivers the laser power necessary to make the incision at the treatment site and simultaneously stimulate tissue healing. Main operating beam 306 is projected onto skin surface 310 to begin incision 308. Simultaneously, beam 304 is also projected onto the site to enhance the healing process. Arrow 312 points in the direction that treatment will be administered. Therefore, main operating beam 306 first makes incision 308 as the device is passed over skin surface 310. The surgical, cutting action is followed by biostimulating beam 304 which stimulates healing.

A later view in time is shown to the lower right of the first, indicating progression of the treatment. It shows optical fiber 302 traveling along skin surface 310 in the direction indicated by arrow 312. Main operating beam 306 has effectively cut incision 308 in the desired area. Furthermore, stimulating beam 304 has stimulated the lased tissue to expedite the healing process. As can be seen from this embodiment, the orientation of optical fiber 302 for this application is important. The procedure would not be as successful if for instance fiber 302 was mistakenly turned so that main operating beam 306 followed biostimulating beam 304 instead of preceding it. Similarly, if for instance fiber 302 was incorrectly turned so that main operating beam 306 and biostimulating beam 304 traveled side by side along the treatment site.

Figure 4:
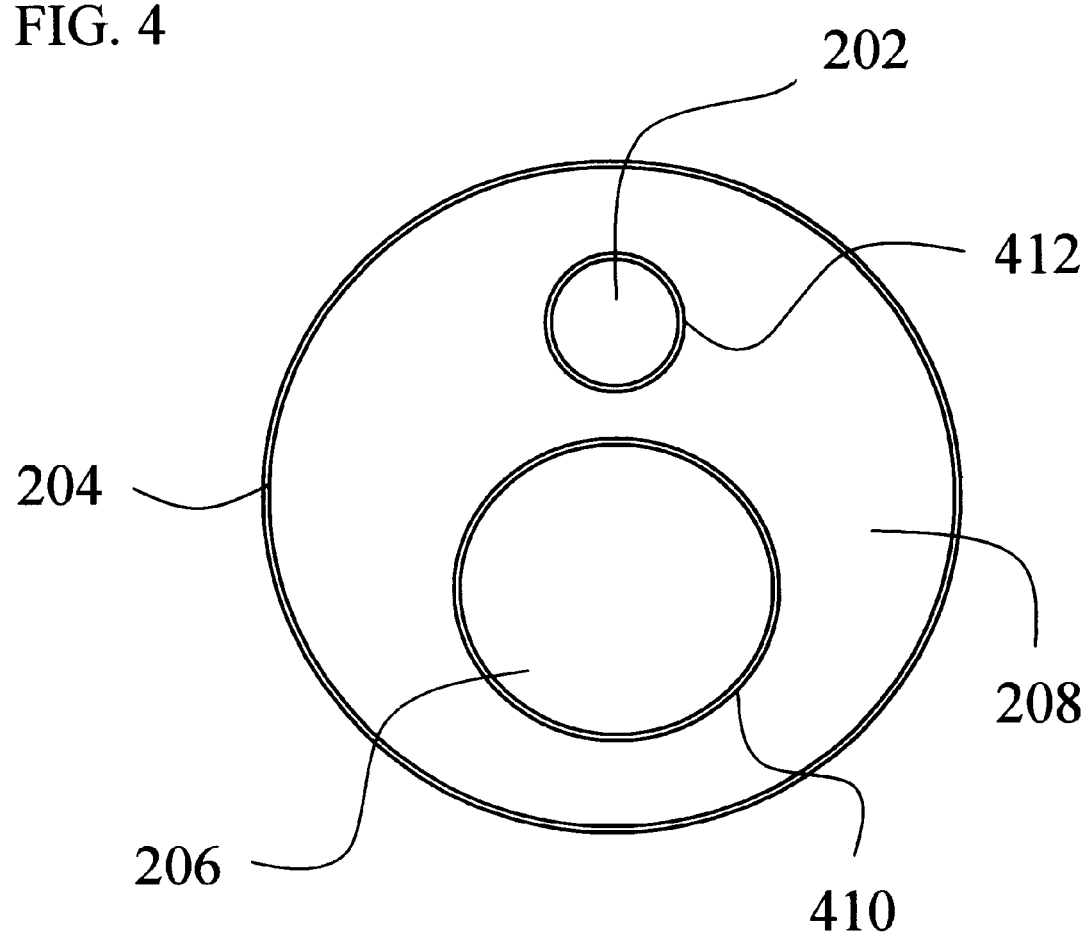
FIG. 4 is a cross-sectional diagram illustrating an alternative variation of the embodiments of FIG. 2.

Obtaining varying NA values in two cores within the same fiber may also be accomplished by placing additional, separate and distinct cladding layers around each core. The cladding layers would each have a different index of refraction thereby allowing for differing NA values. FIG. 4 shows a variation of the embodiment illustrated in FIG. 2. What is shown in FIG. 4 is meant to extend to all embodiments included in FIG. 2. FIG. 4 shows an embodiment of the output structure wherein it is comprised of a multi-core fiber with fiber jacket 204 surrounding cladding layer 208. Embedded in cladding layer 208 and running parallel to the axis of the multi-core fiber are two solid cores, 202 and 206. Core 202 is surrounded by first core cladding layer 410. Core 202 is surrounded by second core cladding layer 412. First core cladding layer 410 and second core cladding layer 412 are separate and distinct. First core cladding layer 410 and second core cladding layer 412 are composed of different materials such that the index of refraction of first core cladding layer 410 is higher than the index of refraction of second core cladding layer 412.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. A laser delivery system combining delivery of a primary surgical/activating laser energy and of a lower power biomodulating laser energy, aimed at biostimulating/biosupressing cellular proliferation as required at a treatment site to enhance wound healing comprising:
    at least two distinct laser sources;
    a first laser source emitting high-power laser energy for performing laser surgical/activation functions;
    a second laser source emitting a low-power laser energy for performing biomodulating functions including biostimulation, biosupression and immunostimulation;
    a first optical fiber and a second optical fiber, each having a proximal end and a distal end;
    an optical coupler with an input end and an output end;
    wherein said first optical fiber's proximal end is optically connected to said first laser source and said first optical fiber's distal end is optically connected to said optical coupler's input end, and wherein said second optical fiber's proximal end is optically connected to said second laser source and said second optical fiber's distal end is optically connected to said optical coupler's input end;
    an optical output structure with a proximal end and a distal end; passing through a hand piece; wherein said hand piece maintains a fixed orientation of said optical output structure during treatment; and
    wherein said high-power laser energy passing through said first optical fiber is coupled to said proximal end of said output structure at said output end of said optical coupler and said low-power laser energy passing through said second optical fiber is coupled to said proximal end of said output structure at said output end of said optical coupler, and wherein said high power energy and low power energy have independent/exclusive optical paths to said distal end of said output structure, from which high power and low power energy beams are projected.

2. A laser delivery system according to claim 1, wherein said optical output structure is a multi-core optical fiber having a first core set off center in said multi-core optical fiber, delivering high-power laser energy, and a second core set off center in said multi-core optical fiber, delivering low-power laser energy.

3. A laser delivery system according to claim 1, wherein said optical output structure is a multi-core optical fiber having a first core set centrally in said multi-core optical fiber, delivering high-power laser energy, and multiple peripheral cores optically coupled through said optical coupler to deliver said second source's low-power laser energy.

4. A laser delivery system according to claim 2, wherein said first core is surrounded by a first core cladding layer and said second core is surrounded by a second core cladding layer.

5. A laser delivery system according to claim 3, wherein said first core is surrounded by a first core cladding layer and said multiple peripheral cores are each individually surrounded by a second core cladding layer.

6. A laser delivery system according to claim 1, wherein said optical output structure is comprised of at least two optical fibers oriented in a fixed manner relative to each other, in which a first fiber is optically coupled to said output of said first laser and said second fiber(s) is optically coupled to said output of said second laser.

7. A laser delivery system according to claim 1, wherein said low-power laser energy, from said second laser source, is emitted at 635 nm for optimal biostimulating effects.

8. A treatment method for a low-power biomodulation and in the same application effecting a high-power laser surgical/activation procedure comprising the steps of:

orienting an optical output structure such that said high-power surgical or activation laser energy is aimed at a treatment site;

orienting said optical output structure such that said low-power biomodulating laser energy is aimed at said treatment site;

moving said optical output structure parallel to a skin surface along said treatment area; and positioning said optical output structure during application such that said high-power laser energy is generally first administered to said treatment site, followed by said low-power laser energy.

9. A treatment method according to claim 8, wherein said low-power laser energy is emitted circumferentially around said high-power laser energy such that positioning of said low-power laser energy relative to said high-power laser energy is fixed at any orientation.

* * * * *